United States Patent
Xie et al.

(10) Patent No.: US 7,414,729 B2
(45) Date of Patent: Aug. 19, 2008

(54) SYSTEM AND METHOD FOR COHERENT ANTI-STOKES RAMAN SCATTERING ENDOSCOPY

(75) Inventors: Xiaoliang Sunney Xie, Lexington, MA (US); Francois Légaré, Belmont, MA (US); Feruz Ganikhanov, Annandale, NJ (US); Conor Evans, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 130 days.

(21) Appl. No.: 11/403,075

(22) Filed: Apr. 12, 2006

(65) Prior Publication Data

US 2007/0088219 A1   Apr. 19, 2007

Related U.S. Application Data

(60) Provisional application No. 60/726,319, filed on Oct. 13, 2005.

(51) Int. Cl.
G01B 9/02 (2006.01)
(52) U.S. Cl. .................................... 356/484
(58) Field of Classification Search ............. 356/128, 356/301, 432, 451, 484, 517
See application file for complete search history.

(56) References Cited

U.S. PATENT DOCUMENTS

| | | | |
|---|---|---|---|
| 4,405,237 A | 9/1983 | Manuccia et al. | |
| 6,108,081 A | 8/2000 | Holtom et al. | |
| 6,151,522 A | 11/2000 | Alfano et al. | |
| 6,294,775 B1 | 9/2001 | Seibel et al. | |
| 6,370,422 B1 | 4/2002 | Richards-Kortum et al. | |
| 6,798,507 B2 | 9/2004 | Xie et al. | |
| 6,809,814 B2 | 10/2004 | Xie et al. | |
| 6,856,712 B2 | 2/2005 | Fauver et al. | |
| 6,934,020 B2 | 8/2005 | Shimada | |
| 6,975,898 B2 | 12/2005 | Seibel | |
| 7,068,878 B2 | 6/2006 | Crossman-Bosworth et al. | |
| 7,277,178 B2 * | 10/2007 | Shpantzer et al. | 356/451 |
| 7,285,089 B2 | 10/2007 | Viellerobe et al. | |

(Continued)

FOREIGN PATENT DOCUMENTS

WO   2004093669   11/2004

OTHER PUBLICATIONS

Legare et al., "Towards an integrated coherent anti-stokes Raman scattering (CARS) microscopy system" Proc. of SPIE vol. 5971, XP-002453520, pp. 597108-1-597108-9.

(Continued)

*Primary Examiner*—Michael A Lyons
(74) *Attorney, Agent, or Firm*—Gauthier & Connors LLP (57) ABSTRACT

A system is disclosed for detecting a signal field from a sample volume. The system includes a source system and an optical fiber system. The source system provides a first electromagnetic field at a first frequency and a second electromagnetic field at a second frequency that is different from the first frequency. The optical fiber system includes at least one optical fiber for guiding the first and second electromagnetic fields to the sample volume to generate coherent radiation characteristic of molecular vibrations by non-linear interaction of the first and second fields with the sample volume. The optical fiber system also receives the signal field resulting from the coherent radiation, and guides the signal field to a detector.

26 Claims, 6 Drawing Sheets

U.S. PATENT DOCUMENTS

| | | | |
|---|---|---|---|
| 7,336,990 | B2 | 2/2008 | Genet et al. |
| 2004/0122328 | A1 | 6/2004 | Wang et al. |
| 2004/0254474 | A1 | 12/2004 | Seibel et al. |
| 2005/0008311 | A1* | 1/2005 | Farroni et al. ............... 385/123 |
| 2005/0173817 | A1 | 8/2005 | Fauver et al. |
| 2005/0242298 | A1 | 11/2005 | Genet et al. |
| 2006/0056017 | A1 | 3/2006 | Berier et al. |
| 2006/0195014 | A1 | 8/2006 | Seibel et al. |
| 2008/0029711 | A1 | 2/2008 | Viellerobe et al. |
| 2008/0045848 | A1 | 2/2008 | Lacombe et al. |

OTHER PUBLICATIONS

Heinrich et al., "Wide-field coherent anti-Stokes Raman scattering microscopy" Applied Physics Letters, vol. 84, No. 5, Feb. 2, 2004, 2004 American Institute of Physics, pp. 816-818.

Wang et al., "Coherent Anti-Stokes Raman Scattering Imaging of Axonal Myelin in Live Spinal Tissues," Biophysical Journal, vol. 89, Jul. 2005, pp. 581-591.

N. Bloembergen, "A Quarter century of stimulated Raman scattering," Pure & Appl. Chem,, vol. 59, No. 10, 1987, pp. 1229-1236.

Petrov et al., "Enhancing red-shifted white-light continuum generation in optical fibers for applications in nonlinear Raman microscopy," Optics Express, vol. 13, No. 4, Feb. 21, 2005, pp. 1299-1306.

Ouzounov et al., "Delivery of nanojoule femtosecond pulses through large-core microstructures fibers," Optics Letters, vol. 27, No. 17, Sep. 1, 2002, pp. 1513-1515.

Silberberg et al., "Optical instabilities in a nonlinear Kerr medium," J. Opt. Soc. Am. B, vol. 1, No. 4, Aug. 1984, pp. 662-670.

Zipfel et al., "Nonlinear magic: multiphoton microscopy in the biosciences," Nature Biotechnology, vol. 21, No. 11, Nov. 2003, pp. 1369-1377.

G.J. Thomas, Jr., "Raman Spectroscopy of Protein and Nucleic Acid Assemblies," Annu. Rev. Biophys. Biomol. Struct. 1999, 28, pp. 1-27.

Puppels et al., "Studying single living cells and chromosomes by confocal Raman microspectroscopy," Nature, vol. 347, Sep. 20, 1990, pp. 301-303.

Romer et al., "Histopathology of Human Coronary Atherosclerosis by Quantifying Its Chemical Composition With Raman Spectroscopy," American Heart Association, Inc. 1998, 97, pp. 878-885.

Hopt et al., "Highly Nonlinear Photodamage in Two-Photon Fluorescence Microscopy," Biophysical Journal, vol. 89, Apr. 2001, pp. 2029-2036.

Denk et al., "Two-Photon Laser Scanning Fluorescence Microscopy," Science, vol. 248, Apr. 6, 1990, pp. 73-76.

Zumbusch et al., "Three-dimensional Vibrational Imaging by Coherent Anti-Stokes Raman Scattering," Physical Review Letters, vol. 82, No. 20, May 17, 1999, pp. 4142-4145.

Potma et al., "Heterodyne coherent anti-Stokes Raman scattering (CARS) imaging," Optics Letters, vol. 31, No. 2, Jan. 15, 2006, pp. 241-243.

Evans et al., "Chemical imaging of tissue in vivo with video-rate coherent anti-Stokes Raman scattering microscopy," PNAS, vol. 102, No. 46, Nov. 15, 2005, pp. 16807-16812.

Cheng et al., Laser-Scanning Coherent Anti-Stokes Raman Scattering Microscopy and Applications to Cell Biology, Biophysical Journal, vol. 83, Jul. 2002, pp. 502-509.

Nan et al., "Nonperturbative Chemical Imaging of Organelle Transport in Living Cells with Coherent Anti-Stokes Raman Scattering Microscopy," Biophysical Journal, vol. 91, Jul. 2006, pp. 728-735.

Ganikhanov et al., "Broadly tunable dual-wavelength light source for coherent anti-Stokes Raman scattering microscopy," Optics Letters, vol. 31, No. 9, May 1, 2006, pp. 1292-1294.

Herz et al., "Micromotor endscope catheter for in vivo, ultrahigh-resolution optical coherence tomography," Optics Letters, vol. 29, No. 19, Oct. 1, 2004, pp. 2261-2263.

Cheng et al., "Coherent Anti-Stokes Raman scattering Microscopy: Instrumentation, Theory, and Applications," J. Phys. Chem. B, 108, pp. 827-840.

Potma et al., "CARS Microscopy for Biology and Medicine," Optics & Photonics News, Nov. 2004, pp. 41-45.

Shafer-Peltier et al., "Raman microspectroscopic model of human breast tissue: implications for breast cancer diagnosis in vivo," Journal of Raman Spectroscopy, 2002, 33, pp. 552-563.

Evans et al., "Coherent anti-Stokes Raman scattering spectral interferometry determination of the real and imaginary components of nonlinear susceptibility x(3) for vibrational microscopy," Optics Letters, vol. 29, No. 24, Dec. 15, 2004, pp. 2923-2925.

Potma et al., "High-sensitivity coherent anti-Stokes Raman scattering microscopy with two tightly synchronized picosecond lasers," Optics Letters, vol. 27, No. 13, Jul. 1, 2002, pp. 1168-1170.

Tearney et al., "Scanning single-mode fiber optic catheter-endoscope for optical coherence tomography," Optics Letters, vol. 21, No. 7, Apr. 1, 1996, pp. 543-545.

Legare et al., "Towards CARS Endoscopy," Optics Express, vol. 14, No. 10, May 15, 2006, pp. 4427-4432.

Huang et al., "Optical Coherence Tomography," Science, vol. 254, Nov. 22, 1991, pp. 1178-1181.

Volkmer et al., "Vibrational Imaging with High Sensitivity via Epidetected Coherent Anti-Stokes Raman Scattering Microscopy," Physical Review Letters, vol. 87, No. 2, Jul. 9, 2001, pp. 023901-1 to 023901-4.

* cited by examiner

SYSTEM AND METHOD FOR COHERENT ANTI-STOKES RAMAN SCATTERING ENDOSCOPY

The present application claims priority to U.S. Provisional Patent Application Ser. No. 60/726,319 filed Oct. 13, 2005.

This invention was sponsored by NIH grants OD000277 and GM062536 and the government has certain rights to this invention.

BACKGROUND OF THE INVENTION

The invention relates to the field of vibrational imaging analysis, and relates in particular to the field of coherent anti-Stokes Raman scattering analysis.

Coherent anti-stokes Raman scattering (CARS) imaging provides for the analysis of chemical and biological samples by using molecular vibrations as a contrast mechanism. In particular, CARS analysis uses at least two laser fields, a pump electromagnetic field with a center frequency at $\omega_p$ and a Stokes electromagnetic field with a center frequency at $\omega_s$. The pump and Stokes fields interact with a sample and generate a coherent anti-Stokes field having a frequency of $\omega_{as}=2\omega_p-\omega_s$ in the phase matched direction. When the frequency difference, $\omega_p-\omega_s$, is tuned to be resonant with a given vibrational mode, an enhanced CARS signal is observed at the anti-Stokes frequency $\omega_{as}$.

Unlike fluorescence microscopy, CARS microscopy does not require the use of fluorophores (which may undergo photobleaching), since the imaging relies on vibrational contrast of biological and chemical materials. Further, the coherent nature of CARS microscopy offers significantly higher sensitivity than spontaneous Raman microscopy. This permits the use of lower average excitation powers and/or short data collection times (which is tolerable for biological samples). The fact that $\omega_{as}>\omega_p, \omega_s$ allows the signal to be detected in the presence of background fluorescence.

For example, U.S. Pat. No. 4,405,237 discloses a coherent anti-Stokes Raman spectroscopic imaging device in which two laser pulse trains of different wavelengths, temporally and spatially overlapped, are used to simultaneously illuminate a sample. The '237 patent discloses a non-collinear geometry of the two laser beams and a detection of the signal beam in the phase matching direction with a two-dimensional detector, which gives the spatial resolution.

A collinear excitation geometry is proposed in U.S. Pat. No. 6,108,081, which discloses a method and apparatus for microscopic vibrational imaging using coherent anti-Stokes Raman scattering in which collinear pump and Stokes beams are focused by a high numerical aperture (NA) objective lens. The nonlinear dependence of the signal on the excitation intensity ensures a small probe volume of the foci, allowing three-dimensional sectioning across a relatively thick sample. The signal beam is detected in the forward direction.

Following the previous non-collinear excitation geometry however, U.S. Pat. No. 6,934,020 discloses a laser microscope in which pump and Stokes beams are delivered from a light emitting system to a beam irradiating mechanism using an optical fiber. The pump and Stokes beams are combined prior to entering a proximal end of the optical fiber, and then separated again into two beams by the beam irradiating mechanism after leaving the distal end of the optical fiber so that each beam may be directed toward each other at a sample. The CARS signal is detected from the sample in the forward direction.

There is also a non-resonant contribution to the CARS signal, however, that does not carry chemically-specific information that can distort and even overwhelm the resonant signal of interest. The CARS background is caused by electronic contributions to the third order nonlinear susceptibility. The non-resonant contribution arises from both the sample of interest as well as of the surrounding isotropic bulk medium (i.e., solvent), and is independent of the Raman shift, $\omega_p-\omega_s$. This non-resonant contribution provides background with no vibrational contrast from which the desired signal must be filtered or somehow distinguished. The presence of this background from the isotropic bulk water has hindered efforts to increase the sensitivity of CARS imaging, particularly in biological applications.

One approach to reducing the non-resonant background field in CARS spectroscopy is to take advantage of the fact that the non-resonant background has different polarization properties than the resonant signal. For example, U.S. Pat. No. 6,798,507 discloses a system in which the pump and Stokes beams are polarized, and a polarization sensitive detector is employed. In high resolution CARS microscopy, however, tightly focused collinear excitation beams are sometimes necessary and it is known that tightly focusing polarized beams will result in polarization scrambling.

U.S. Pat. No. 6,809,814 discloses a system in which a CARS signal is received in the reverse direction (epi-direction) from the sample. The signal generated in the epi-direction typically includes a significantly higher signal to background ratio, but in some applications, the signal generated in the epi-direction is usually much smaller than that generated in the forward direction.

In addition, conventional CARS microscopy systems generally require that a sample be extracted from a subject and examined, typically while positioned on a stage that may be movable in x and y directions. In certain applications, however, it is desirable to perform CARS analysis of a sample in situ. Such samples, however, may not be easily viewed using forward direction CARS.

There is a need, therefore, for a system and method for providing applications of CARS analyses in situ within a human, animal or other subject or sample.

SUMMARY

The invention provides a system for detecting a signal field from a sample volume. The system includes a source system and an optical fiber system. In accordance with an embodiment, the source system provides a first electromagnetic field at a first frequency and a second electromagnetic field at a second frequency that is different from the first frequency. The optical fiber system includes at least one optical fiber for guiding the first and second electromagnetic fields to the sample volume to generate coherent radiation characteristic of molecular vibrations by non-linear interaction of the first and second fields with the sample volume. The optical fiber system also receives the signal field resulting from the coherent radiation, and guides the signal field to a detector. In accordance with other embodiments, the system further includes a scanning system for providing a pump field and a Stokes field to a plurality of focal areas in the sample volume In accordance with another embodiment, the invention provides a coherent anti-Stokes Raman scattering endoscopy system for detecting an anti-Stokes field induced by a non-linear interaction of a plurality of optical frequency components of at least one excitation pulse train in a sample volume. The system includes a source system and an optical fiber system. The source system includes a coherent source for providing the plurality of optical frequency components of at least one excitation pulse train. The optical fiber system includes at least one optical fiber for receiving an anti-Stokes field from the sample volume, and for guiding the anti-Stokes field to a detector using the at least one optical fiber in the optical fiber system. The anti-Stokes field is generated responsive to a non-linear coherent interaction of the plurality of optical frequency components with the sample volume.

In accordance with a further embodiment, the invention provides a coherent anti-Stokes Raman scattering endoscopy system for detecting an anti-Stokes field induced by a non-linear interaction of a pump field and a Stokes field in a sample volume. The system includes a source system, a pump and Stokes field optical fiber system, and an anti-Stokes field optical transmission system. The source system provides a pump electromagnetic field at a pump frequency and a Stokes electromagnetic field at a Stokes frequency that is different from the pump frequency. The pump field and Stokes field optical fiber system includes an optical fiber for guiding the pump and Stokes fields toward a lens as a single beam. The lens is for directing the pump field and the Stokes field into the sample volume. The anti-Stokes field optical transmission system receives the anti-Stokes field from the sample volume, and directs the anti-Stokes field to a detector. The anti-Stokes field is generated responsive to a non-linear coherent field generated by the interaction of the pump and Stokes fields in the sample volume.

BRIEF DESCRIPTION OF THE DRAWINGS

The following description may be further understood with reference to the drawings in which.

The drawings are shown for illustrative purposes only and are not to scale.

DETAILED DESCRIPTION

For many analytical applications in biomedicine, it is desirable to perform tissue imaging in situ. Endoscopic techniques have been widely used in medicine for applications including surgical interventions and disease diagnosis. Endoscopy has been carried out with contrast based on optical coherence tomography (OCT), one and two-photon fluorescence, and second harmonic generation. These advances have lead to immediate applications in clinical environments. While OCT has been very successful for imaging tissue morphology, its contrast is based on refractive index differences. Endogenous fluorescence endoscopy is sensitive to intrinsic biological fluorophores, which limits it generality. Second harmonic generation endoscopy is sensitive to non-centrosymmetric structures, but its application is limited to few biological materials. A CARS endoscope would offer label-free chemically-selective imaging in situ, making it an ideal tool for biomedical applications.

It has been discovered that the benefits of coherent anti-Stokes Raman scattering analysis may be realized in an endoscopic system capable of imaging specimens with submicron lateral resolution and resolution in the axial direction on the order of tens of microns down to several microns. The invention provides that an optical fiber may be used to not only deliver pump and Stokes fields as a single beam to a sample directly, but that the CARS signal may be detected in the epi-direction back through the optical fiber. In particular, applicants have found that although a pump beam (e.g., 800 nm) and a Stokes beam (e.g., 1,064 nm) may be provided through a single mode fiber, designed 830 nm propagation for example), the CARS signal that is produced may also be transmitted back through the same fiber even though its wavelength (e.g., 660 nm) is far shorter than that of the pump and Stokes beams. Although the CARS signal is outside of the single mode range of the fiber, the multimode transmission provided by the fiber for the CARS signal is sufficient for CARS endoscopy. Also, although the sample may provide heterogenous scattering of the anti-Stokes response, the initially forward propagating anti-Stokes field that is re-directed backward by multiple scattering events the turbid material in situ may be captured and directed toward a detector that is outside the body. In other embodiments, fields in addition to pump and Stokes fields may be used to generate an anti-Stokes signal (e.g., a probe frequency field). In further embodiments, the anti-Stokes field may be generated using a plurality of optical frequency components of at least one excitation pulse train in a sample volume, such as may result from a broadband pulsed laser system.

Figure 1:
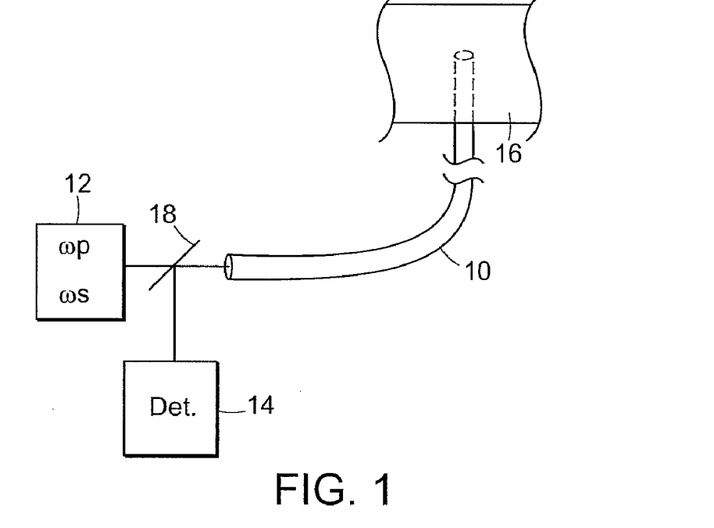
FIG. 1 shows an illustrative diagrammatic view of a system in accordance with an embodiment of the invention.

As shown in FIG. 1, a system in accordance with an embodiment of the invention may include an optical fiber system 10, a source 12 for providing a pump field and a Stokes field, and a detector 14. The source 12 (such as an optical parametric oscillator) directs the collinear pump and Stokes fields toward a sample within a patient 16 via the optical fiber system 10. The back-scattered anti-Stokes field is detected back through the optical fiber system 10 at the detector 14 via a beam splitter 18.

Figure 2:
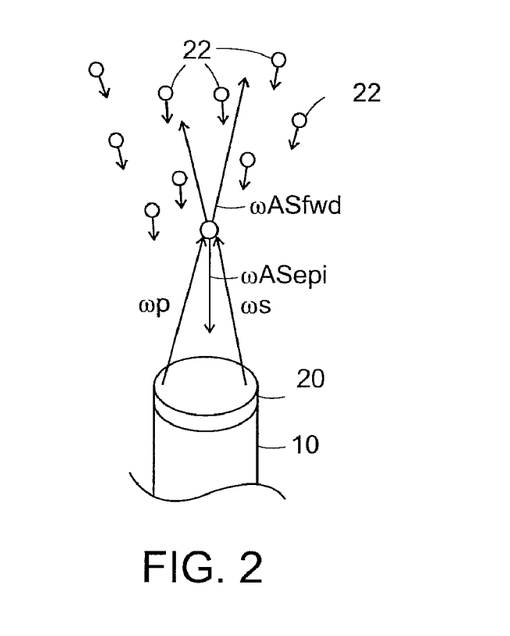
FIG. 2 shows an illustrative diagrammatic view of a distal portion of the system shown in FIG. 1.

Applicants have found that in certain samples, such as a tissue of a patient in situ, a strong epi-CARS signal is produced that is due not only to the initial non-linear scattering in the epi-direction, but also predominantly due to multiple linear scattering events of the forward-propagating anti-Stokes signal in turbid inhomogeneous media. The forward propagating CARS signal can be redirected into the same direction as the initially epi-directed signal component by means of multiple scattering events in the tissue. This is illustrated in FIG. 2 in which the pump field ($\omega_p$) and Stokes field ($\omega_s$) pass through the optical fiber system 10 and objective lens 20 as a single beam. The third order non-linear vibrational response of the sample then produces a forward directed anti-Stokes field ($\omega_{as,fwd}$) and a generally weaker epi-directed anti-Stokes field ($\omega_{as,epi}$). A significant portion of the forward directed anti-Stokes field is scattered off of other material 22, and this scattered anti-Stokes field and the epi-directed anti-Stokes field are collected by the lens 20 and carried by the optical fiber system 10 back to a proximal end of the optical fiber system to a detector. The multiple scattering events, therefore, provide a mechanism for detecting a CARS signal in the backward direction through an optical fiber system. Because the nonlinear CARS signal is only generated where the intensity is the highest, the backward detected CARS signal that is transmitted through the fiber only originates in the small focal volume that is interrogated despite the backward scattering of the forward CARS signal occurring in a much larger volume.

In a CARS endoscope system in accordance with an embodiment of the invention, two high-peak power pulses at different wavelengths need to be delivered to the focusing optics and scanning head without a significant spectral broadening. The generated anti-Stokes pulse is at a wavelength shorter than the excitation wavelengths and needs to be efficiently collected and propagated back into the same fiber. This CARS endoscope optical design should ensure that the pump and the Stokes laser pulses are overlapped spatially and temporally in the sample using a tight focusing geometry. Spatial overlap is non-trivial because of the presence of chromatic aberrations (due to lenses' material dispersion) and other types of aberrations. Specially designed micro-optic lenses are required that focus both the pump and Stokes beam to ensure that the focal spots for the pump and Stokes beams are as coincident as possible.

In a CARS endoscope system in accordance with another embodiment of the invention, a plurality of optical frequencies can be used to generate an anti-Stokes signal. In one possible configuration, a pump field and Stokes field can be combined with a probe field to generate the anti-Stokes signal. The pump, Stokes and probe fields can be from either narrowband or broadband pulses. In another possible configuration, a single broadband pulse can be used to generate an anti-Stokes signal. This single broadband pulse can be modified using amplitude or phase modulators such as a spatial light modulator. Another configuration can include a narrowband pump and broadband Stokes pulse for multiplex CARS measurements. This configuration can also incorporate a narrowband probe field for generating an anti-Stokes signal.

A scanning mirror design may also be used in certain embodiments as discussed in more detail below, as well as a broadly tunable optical parametric oscillator for simultaneously delivering pump and Stokes pulses. The pump and Stokes beams could be propagated in a single mode fiber or in a photonic crystal fiber. Aspheric lenses may be used for collimation of the light after the fiber and focusing of the light onto a sample, and scanning may be achieved using, for example, a micro- electromechanical switch (MEMS) mirror for two dimensional scanning of the beams across the sample. The collection and coupling into the fiber of the signal at the anti-Stokes wavelength may be accomplished through the use of aspheric lenses.

The endoscope may be coupled within or along a catheter to within a patient. The pump and Stokes fields may also be provided using a scanning head to position the pump and Stokes fields at desired locations in the focal volume as discussed in more detail below. The pump and Stokes fields may be directed through the optical fiber system using a single mode optical fiber, and the coupled light at the anti-Stokes wavelength may experience single- or multimode propagation in the fiber system. The propagated light may be demultiplexed by an additional fiber port that is fused to the fiber or outcoupled by a dichroic mirror at the input end of the fiber. The demutiplexed or outcoupled light signal is filtered out from stray light at other optical frequencies and detected with sensitive and high electric gain photodetector. The electrical signal is conditioned and digitized and its value is read out synchronously with movement of the scanning elements such as a MEMS mirror, thus producing an image.

The invention, therefore, provides a CARS endoscope. In certain embodiments, the design utilizes a single mode optical fiber with a focusing unit attached to the distal end. Picosecond pump and Stokes pulse trains in the near infrared are delivered through the fiber with nearly unaltered spectral and temporal characteristics at intensities needed for endoscopy. CARS endoscopic images are recorded by raster scanning the fiber with respect to the sample and collecting the epi-CARS signal generated at the specimen. Endoscopes of the invention may be well suited for in situ high sensitivity CARS imaging for biomedical applications offering many advantages, including (i) chemical contrast based on Raman vibrational spectroscopy, (ii) high sensitivity and rapid acquisition rates due to the coherent nature of the CARS process, (iii) and sub-wavelength 3D spatial resolution.

As mentioned above, the CARS process requires two laser frequencies, called pump ($\omega_p$) and Stokes ($\omega_s$) frequencies. When the difference frequency of the two laser frequencies is set to that of a vibrational resonance of a sample, a strong optical response occurs at the anti-Stokes frequency ($\omega_{as}=2\omega_s-\omega_p$). The CARS signal is derived from the third-order nonlinear susceptibility, $\chi^{(3)}$, of a material, which is significantly enhanced when the difference frequency is tuned into a resonance. For imaging, CARS requires high peak power pulse trains from laser sources capable tunable over a wide range, so that the difference frequency can cover the entire vibrational spectrum. Tunable picosecond sources have been found to be optimal for imaging applications as they achieve high spectral resolution and optimal signal to background ratios. Synchronously pumped and broadly tunable optical parametric oscillators (OPO) are ideal sources for this purpose. For such laser pulses, it has been shown that is possible to deliver the beams to a microscope without affecting the temporal and spectral domain characteristics for 1 meter length single-mode fiber.

Figure 3:
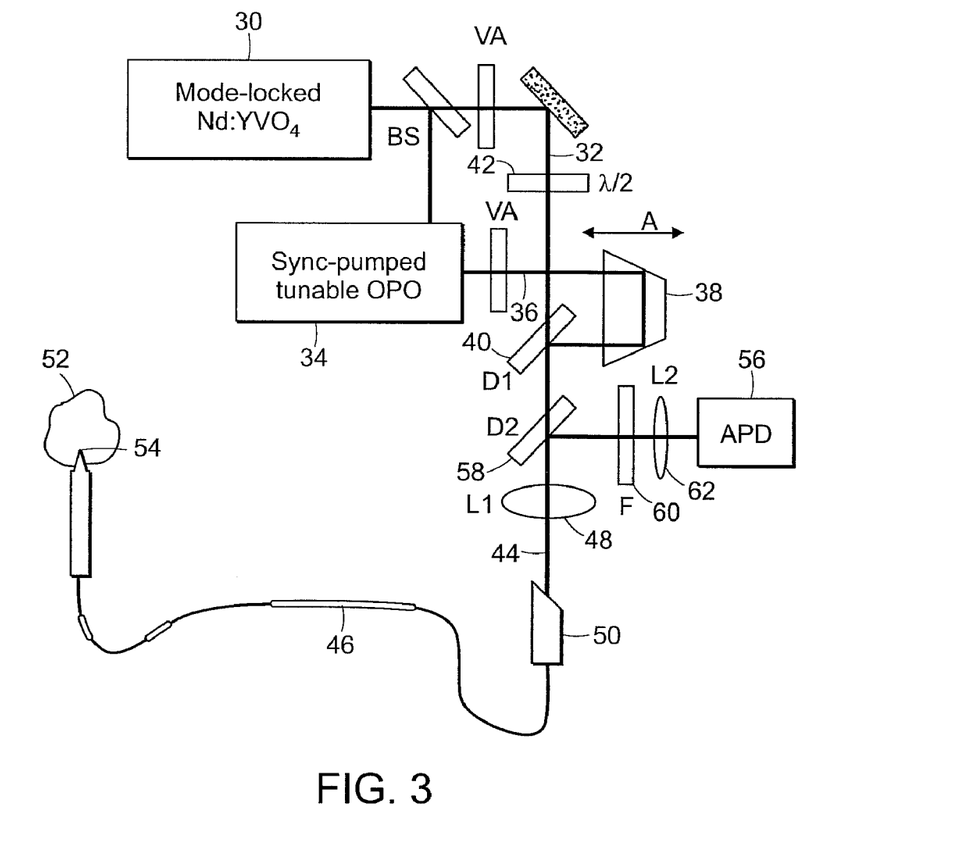
FIG. 3 shows an illustrative diagrammatic view of a system in accordance with another embodiment of the invention.

As shown in FIG. 3, a endoscope system in accordance with an embodiment of the invention includes a mode locked Nd:YVO4 laser 30, a Stokes field beam 32 and a synchronous-pumped tunable optical parametric oscillator (OPO) 34 that provides a pump field beam 36. The system also includes a delay unit 38 that adjusts the timing (by moving as indicated at A) between the pump and Stokes field beams prior to being combined by a dichroic mirror 40 (D1). The path of the Stokes beam also includes a half waveplate ($\lambda/2$) 42 as well.

In particular, the laser source system includes the laser 30, which may be a passively mode-locked Nd:YVO$_4$ laser (High-Q Laser Manufacturing, GmbH) operating at 1064.2 nm delivering transform limited 7 ps pulses at a repetition of 76 MHz with 10 W average output power, and the OPO 34. The majority of the Nd:YVO$_4$ output (9 W) was used to synchronously pump the OPO 34 (using a 15% beam splitter). The OPO cavity is configured to resonate on its signal wavelength and utilizes intracavity doubling to efficiently generate up to 2 W of average output power with 5 ps duration pulse trains. Broad wavelength tuning in the 780-920 nm range is achieved by adjusting the position and temperature of a multi-grating periodically poled lithium niobate crystal used for parametric generation and by setting the temperature of the intracavity doubler to maximum power output. A portion of the 1064 nm beam with available average power of ~1.3 W was used as a Stokes beam while the tunable OPO output provided the pump beam. The output beam quality of the Stokes and pump beams are estimated to have $M^2$ factors of ~1.1 and ~1.3, respectively. The pump and Stokes beams are combined on a dichroic mirror (Chroma, 950DCXR) and collinearly propagate to the fiber coupling optics. Variable attenuators were also used in the pump and Stokes beam paths as shown.

The pump field and the Stokes field beams are combined by the mirror 40 to provide a single collinear beam 44. This beam is directed into an optical fiber system 46 using a lens 48 onto an angle-cut fiber end 50 to eliminate back-reflection. The pump field and Stokes fields are then directed into a focal volume 52 of a sample using an objective lens 54 at a distal end of the optical fiber system 46. The anti-Stokes field that is generated is received by the objective lens 54 back through the optical fiber system 54 and lens 48, and is directed by a beam splitter 56 toward a detector 56 such as an avalanche photo diode or a photo multiplier tube via a dichroic mirror beam splitter 58.

The combined laser beam with pump and Stokes fields was coupled by an aspheric lens into a 1-m long step index (0.12 numerical aperture, 5.6 μm mode field diameter at 830 nm), non-polarization maintaining silica fiber (non-PMF) designed for single mode propagation at 830 nm. The fiber bandwidth allows for single mode propagation up to 200 nm above the designed wavelength. The size and divergence of the pump and Stokes beams were adjusted to maximize the coupling efficiency. A wavelength-dependent polarization rotation in the fiber was observed, which is undesirable since the maximum CARS signal is generated when both beams have the same polarization. The half-wave plate 42 was used therefore, in the Stokes beam line to compensate for this polarization rotation in order to optimize CARS signal generation. The delay unit 38 in the line for the pump beam was used before the fiber to overlap the pump and Stokes pulse trains in time. Straight fiber terminals were found to cause significant optical feedback to the Nd:YVO$_4$ laser, necessitating the use an angle-cut fiber terminator 50. The typical coupling efficiency of the beams into the fiber was better than 40%. The focusing lens 48 with a diameter of 4 mm was attached to the distal fiber end that contains an aspheric lens with a diameter of 2.4 mm, a numerical aperture of 0.43, and a working distance of 1.1 mm. In various embodiments, the endoscope may be raster scanned with respect to the sample by a XYZ piezo stage as discussed in more detail below. The backwards-generated fields are collected and focused by the endoscope, propagated back through the fiber and then separated from the excitation beams with the dichroic mirror 58. The CARS signal is filtered with three 670 nm bandpass filters 60 and focused with a 100 mm concave lens 62 onto the avalanche photodiode 56.

Figure 4A:
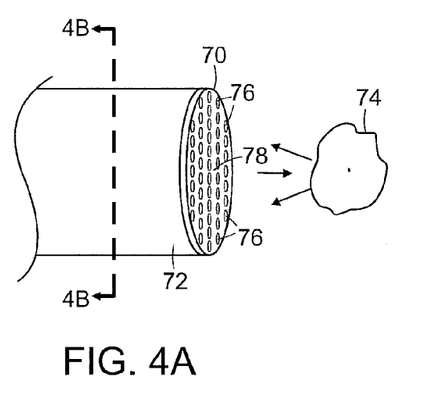
FIG. 4A shows an illustrative diagrammatic view of a distal portion of a system in accordance with another embodiment of the invention.
Figure 4B:
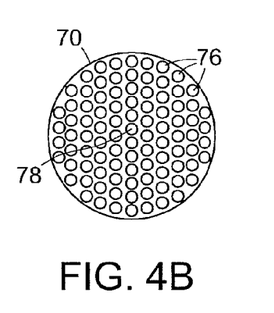
FIG. 4B shows a view of the distal portion of the system of FIG. 4A taken along line 4-4B thereof.

In accordance with various embodiments, the optical fiber system may include a single optical fiber or a bundle of optical fibers. As shown in FIGS. 4A and 4B, the distal end of an optical fiber system may include a lens 70 that focuses illumination from an optical fiber system 72 into a focal volume 74. The optical fiber system may include a plurality of optical fibers 76. In certain embodiments, one of the optical fibers 78 may be a single mode fiber for providing the pump and Stokes fields to the focal volume, and the remaining optical fibers may be single or multimode optical fibers for providing the anti-Stokes field back through the optical fiber system 72. The optical fibers 76 and 78 may be either enclosed in a matrix of a cladding material, or may be sufficiently non-circularly shaped to suppress evanescent energy transfer to neighboring fibers.

Figure 5:
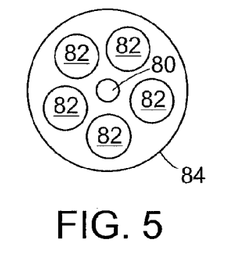
FIG. 5 shows a view similar to that of FIG. 4B of a distal lens for use in a system in accordance with another embodiment of the invention.

In accordance with another embodiment, the optical fiber system may include a single mode optical fiber 80 for providing the pump and Stokes fields, and a plurality of multimode optical fibers 82 of a larger diameter for receiving the anti-Stokes field from the sample volume as shown in FIG. 5. A cladding material 84 may also be used to reduce coupling between the optical fibers.

Figure 6:
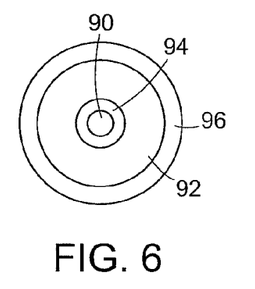
FIG. 6 shows a view similar to that of FIGS. 4B and 5 of a distal lens for use in a system in accordance with a further embodiment of the invention.

In accordance with a further embodiment as shown in FIG. 6, the optical fiber system may include a double clad system including a central single mode optical fiber 90 for providing the pump and Stokes fields, and a multimode optical fiber 94 having an annular cross-section that surrounds the optical fiber 90 for receiving the anti-Stokes field from the sample volume. The system may also include a cladding material 94 between the optical fibers 90 and 92, and a cladding material 96 outside the optical fiber 92.

Figure 7:
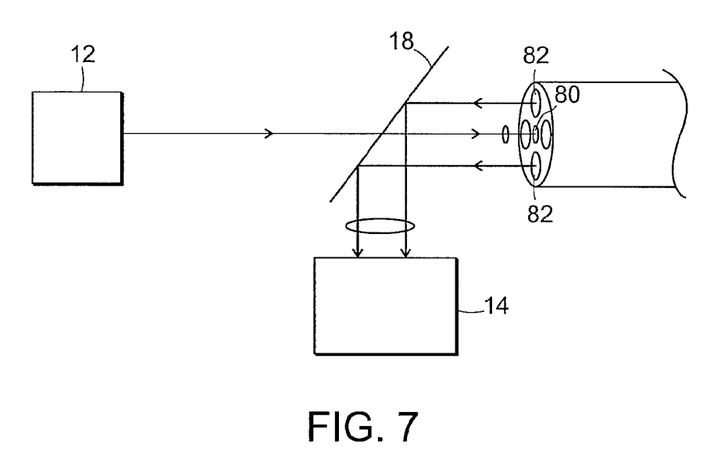
FIGS. 7 and 8 show proximal portions of systems in accordance with further embodiments of the invention.
Figure 8:
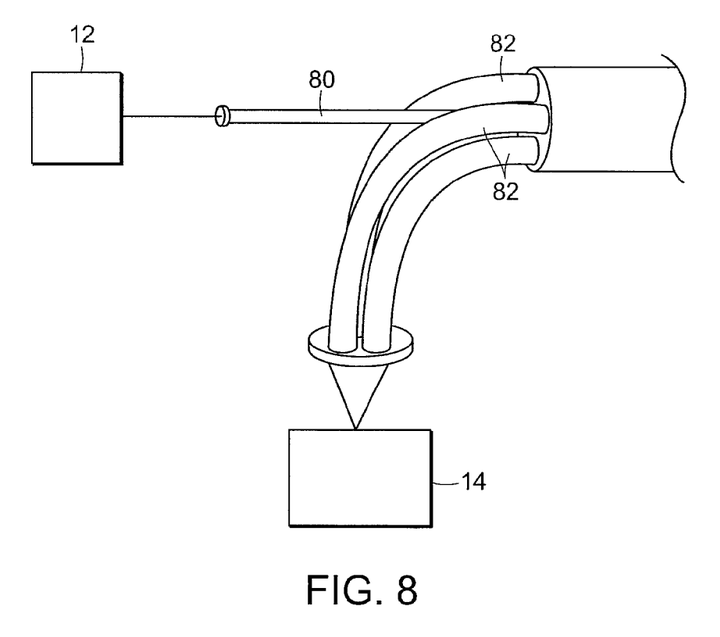

With reference again to the optical fiber system of FIG. 5, a coupling arrangement at the proximal end of the optical fiber system as in FIG. 7 may include the beam splitter 18 that permits the pump and Stokes fields to pass into the optical fiber 80 via a lens, and provides that the anti-Stokes fields from the optical fibers 82 are directed toward the detector 14 via a lens. In accordance with further embodiments as shown in FIG. 8, the optical fiber 80 may be separated from the optical fibers 82 such that the optical fiber 80 may be directly coupled to the laser source 12 via a lens while the optical fibers 82 are directly coupled to the detector 14 via a lens without the need for a beam splitter.

Figure 9:
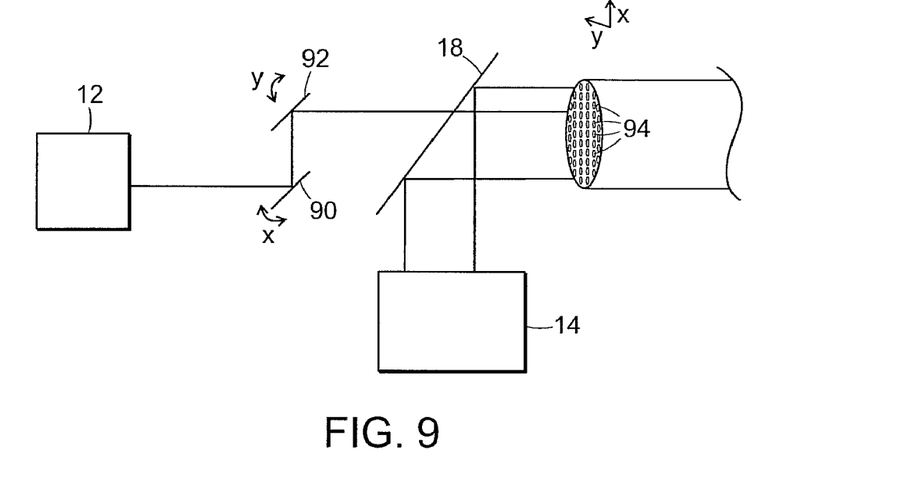
FIGS. 9 and 10 show proximal portions of a system in accordance with further embodiments of the invention that include scanning systems.
Figure 10:
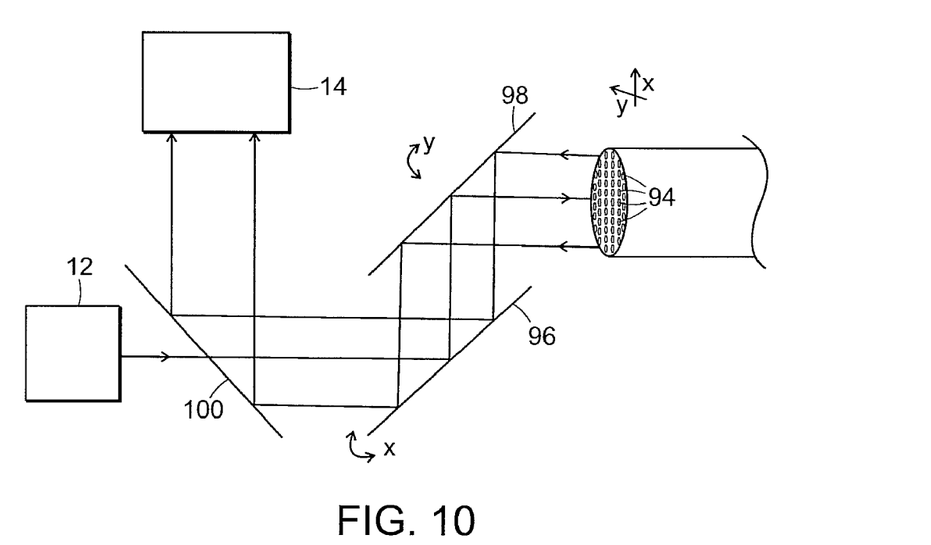

In accordance with further embodiments, the focal position of the pump and Stokes fields may be scanned within a focal volume by a scanning system as the proximal end of the optical fiber. For example, as shown in FIG. 9, x and y position scanning mirrors 90 and 92 may be used to position the beam that includes the pump and Stokes fields onto any of a plurality of single mode optical fibers 94 in an optical fiber system such as shown in FIG. 4B. Irrespective of the optical fiber being used for the pump and Stokes fields, the anti-Stokes field received in the return direction will travel along a number of optical fibers. As shown in FIG. 10, a scanning system in accordance with a further embodiment of the invention may include x and y position mirrors 96 and 98 between a beam splitter 100 (that directs the anti-Stokes field toward the detector 14) and the optical fiber system. The system of FIG. 10 provides that the pump, Stokes and anti-Stokes fields will remain collinear until the anti-Stokes field is directed by the beam splitter 100 toward the detector 14 for a plurality of angular positions of the pump and Stokes fields beam as provided by the mirrors 96 and 98.

Figure 11:
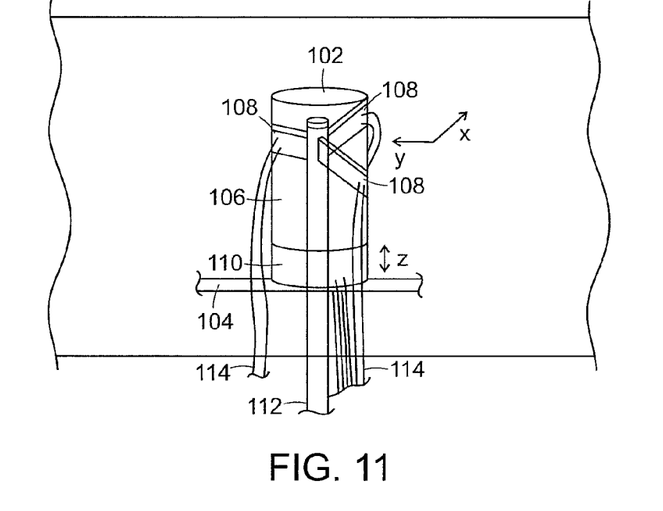
FIG. 11 shows a distal portion of a system in accordance with another embodiment of the invention that includes a scanning system.

In accordance with further embodiments, the focal position of the pump and Stokes fields may be scanned within a focal volume by a scanning system as the distal end of the optical fiber. As shown in FIG. 11, a distal scanning system may include a housing 102 that includes fixed and moving portions 104 and 106 respectively, as well as x and y direction piezoelectric motors 108, and a z axis annular-shaped piezoelectric motor 110. The optical fiber system 112 may then be delivered into the housing 102 and electrical control lines 114 may be brought back to outside of the patient.

The temporal and spectral characteristics for both pump and Stokes pulses may be precisely estimated using the material dispersion, modal refractive index, and nonlinear optical parameters for a fused silica fiber. Temporal broadening for the 5-7 picosecond duration transform limited pulses in the 1 m fiber is negligible and is estimated to be less than 0.1%. Auto- and cross-correlation traces for the two pulses confirm this prediction.

Pulse spectral broadening due to fiber propagation has a large effect on important characteristics of the CARS endoscope, such as spectral resolution and image contrast. Spectral broadening due to self-phase modulation starts to be noticeable when the nonlinear phase shift is on the order of $2\pi$. The per-pulse energy corresponding to this condition can be derived from the formula for the nonlinear phase shift. The result is:

$$\varepsilon_{2\pi} \cong \frac{\pi \lambda t_p D_{eff}^2}{4 n_2 L} \quad (1)$$

where $t_p$–pulsewidth (~6 ps), $D_{eff}$-mode field diameter (~5.6 μm), $n_2$-nonlinear refractive index of silica ($2.6 \times 10^{-16}$ cm²/W), L-fiber length. For a fiber length of 1 m and pulse wavelength centered about 800 nm, the $2\pi$-shift occurs at pulse energies of nearly 4 nJ, which equates to approximately 300 mW average power at a repetition of 76 MHz. The $2\pi$ nonlinear phase shift was observed at average powers of 400 mW and 700 mW for 803.5 nm and 1064.2 nm, respectively. The broadened spectrum for 803.5 nm pulse showed noticeable asymmetry indicating an asymmetric spectral pulse profile from the OPO.

At these pulse energies, propagation through 5 m of fiber resulted in spectral broadening of 40 cm$^{-1}$ and 60 cm$^{-1}$ for 803.5 nm and 1064.2 nm, respectively. This broadening is small and on the same order as characteristic Raman linewidths in liquids. When collecting endoscopic images, we typically used 80 mW of power for both laser beams. This average power is far below the threshold for self-phase modulation induced spectral broadening. Therefore, under our experimental conditions, self-phase modulation is absent, and fiber propagation does not affect the CARS spectral selectivity. The peak power of the oscillators used is over three orders of magnitude lower than the value of critical power for self-focusing of the beam.

Figure 12A:
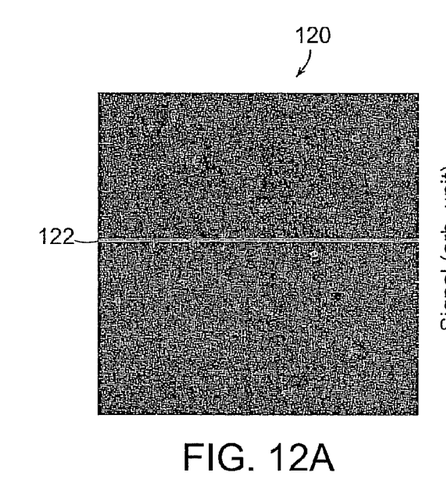
FIGS. 12A and 12B show a photomicrograph and associated graphical representation of an anti-Stokes field obtained by a system in accordance with an embodiment of the invention.
Figure 12B:
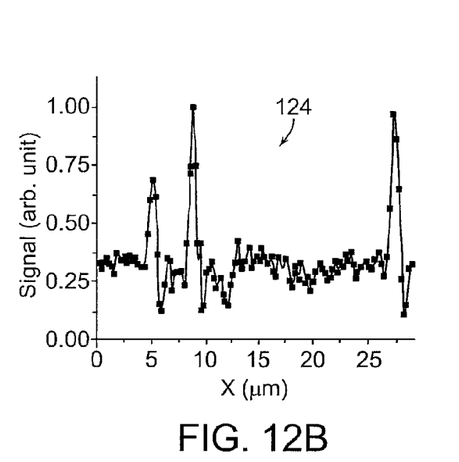

The performance of the CARS endoscope may be characterized by imaging size-calibrated polystyrene beads with the frequency difference between the pump and Stokes beams set to the aliphatic CH band ($\omega_p - \omega_s \sim 2845$ cm-1). FIG. 12A shows at 120 a XY image of clearly resolved 0.75 μm polystyrene beads spin coated on a coverslip. The full width half max value (FWHM) of the beads is determined to be 0.76 μm using a Gaussian fitting for a section 122 of the image as shown at 124. Smaller beads imaged with the endoscope system were calculated to have the same FWHM, setting the maximum lateral resolution to ~0.8 μm. The axial resolution was measured to be ~12 μm using the same procedure. This spatial resolution is expected based on the numerical aperture of the focusing lens and is sufficient for imaging tissue morphology.

The endoscope, therefore, collects epi-CARS signals, which are known to come from three different mechanisms. In thin samples, epi-signal is usually generated only when there is incomplete destructive interference in the backwards direction. This occurs when the size of a resonant object is very small compared to the excitation wavelengths. A second mechanism occurs when there is an abrupt change in the third-order nonlinear susceptibility, which can occur at an interface. A third mechanism can occur in thick samples (>100 μm); multiple scattering events due to the turbidity of the specimen can redirect a fraction of the intense forward CARS signal in the epi-direction. This mechanism has been shown to dominate the epi-CARS signal in tissues such as skin. For thin object like beads (about 5 μm), the epi-CARS signal comes from the first two mechanisms and can be coupled back into the single-mode delivery fiber. For thicker tissue, however, the CARS endoscopy systems disclosed herein should provide sufficient by efficiently coupling the reflected light from the sample. In further embodiments, the focal length can be varied to obtain depth-resolved information from the sample.

Those skilled in the art will appreciate that numerous modifications and variations may be made to the above disclosed embodiments without departing from the spirit and scope of the invention.

What is claimed is:

1. A coherent anti-Stokes Raman scattering endoscopy system for detecting an anti-Stokes signal from a sample volume, said system comprising:
   a source system for providing a pulsed pump field at a first frequency and a pulsed Stokes field at a second frequency that is different from the first frequency, both said pulsed pump field and said pulsed Stokes field being provided at the same pulse repetition rate and synchronous with one another; and
   an optical fiber system including at least one optical fiber, said optical fiber system for guiding said pulsed pump and Stokes fields to the sample volume such that pump pulses and Stokes pulses arrive at the same time in the sample volume to generate third order non-linear coherent radiation characteristic of molecular vibrations by non-linear interaction of the pulsed pump and Stokes fields with the sample volume, for receiving the anti-Stokes signal resulting from the coherent radiation, and for guiding the anti-Stokes signal to a detector, wherein said pulsed pump and Stokes fields are collinearly directed to said sample volume in a single beam that includes said pulsed pump and Stokes fields.

2. The system as claimed in claim 1, wherein the system detects a redirected anti-Stokes signal that results from linear scattering of the coherent radiation by a heterogeneous medium that is outside of a focal volume at which the pump and Stokes pulses arrive at the same time to generate the third-order non-linear coherent radiation.

3. The system as claimed in claim 2, wherein the sample volume is within a tissue of a patient.

4. The system as claimed in claim 1, wherein said optical fiber system includes a plurality of optical fibers.

5. The system as claimed in claim 4, wherein said pulsed pump and Stokes fields are guided to the sample volume using one of the plurality of optical fibers in said optical fiber system, and said anti-Stokes signal is guided to said detector using another optical fiber of said plurality of optical fibers in said optical fiber system.

6. The system as claimed in claim 1, wherein said anti-Stokes signal is guided to said detector using a plurality of optical fibers in said optical fiber system.

7. The system as claimed in claim 1, wherein said pulsed pump and Stokes fields are guided to the sample volume using a single mode optical fiber in said optical fiber system, and said anti-Stokes signal is guided to said detector using a plurality of multi-mode optical fibers in said optical fiber system.

8. The system as claimed in claim 1, wherein said system further includes a scanning system for selectively directing said pulsed pump and Stokes fields toward any of a plurality of selected optical fibers in said optical fiber system at a proximal end of said optical fiber system.

9. The system as claimed in claim 8, wherein said system includes a beam splitter between said scanning system and said proximal end of said optical fiber system, said beam splitter for directing said anti-Stokes signal toward said detector.

10. The system as claimed in claim 8, wherein said system includes a beam splitter between said source system and said scanning system, said beam splitter for directing said anti-Stokes signal toward said detector.

11. The system as claimed in claim 1, wherein said system further includes a distal scanning system distal from said optical fiber system for selectively directing said pulsed pump and Stokes fields toward any of a plurality of selected focal volumes in said sample volume.

12. A coherent anti-Stokes Raman scattering endoscopy system for detecting an anti-Stokes signal induced by a non-linear interaction of a plurality of optical frequency components of at least one excitation pulse train in a sample volume, said optical frequency components including a pulsed pump electromagnetic field and a pulsed Stokes electromagnetic field, said system comprising:

a source system including a coherent source for providing the pulsed pump electromagnetic field and the pulsed Stokes electromagnetic field of the at least one excitation pulse train, both the pulsed pump electromagnetic field and the pulsed Stokes electromagnetic field being provided at the same pulse repetition rate and synchronous with one another; and an optical fiber system including at least one optical fiber for guiding the pulsed pump and Stokes electromagnetic fields to the sample volume collinearly in a single beam that includes said pulsed pump and Stokes electromagnetic fields such that pump field pulses and Stokes field pulses arrive at the same time in a focal volume in the sample volume, and including at least one other optical fiber for receiving an anti-Stokes signal from the sample volume and for guiding the anti-Stokes signal to a detector using the at least one other optical fiber in said optical fiber system, said anti-Stokes signal being generated responsive to a third-order non-linear coherent field generated by the interaction of said plurality of optical frequency components with the sample volume, and said anti-Stokes signal includes a forward-directed anti-Stokes signal generated within the sample volume in a forward direction that is scattered by material within the sample volume that is outside of the focal volume in a direction that is substantially different from the forward direction.

13. The system as claimed in claim 12, wherein said anti-Stokes signal is guided to said detector using a plurality of optical fibers in said optical fiber system.

14. The system as claimed in claim 12, wherein said optical fiber system includes a double-clad optical fiber.

15. The system as claimed in claim 12, wherein said at least one optical fiber is a single mode fiber and at least one other optical fiber is a multi-mode fiber.

16. The system as claimed in claim 12, wherein said system further includes a proximal scanning system for directing said pulsed pump and Stokes electromagnetic fields toward any of a plurality of selected optical fibers in said optical fiber system at a proximal end of said optical fiber system.

17. The system as claimed in claim 12, wherein said system further includes a distal scanning system for directing said pulsed pump and Stokes electromagnetic fields toward any of a plurality of selected focal volumes in said sample volume.

18. A method of detecting an anti-Stokes signal in a coherent anti-Stokes Raman scattering endoscopy system, said method comprising the steps of:

providing a pulsed pump field at a first frequency and a pulsed Stokes field at a second frequency that is different than the first frequency, both of said pulsed pump field and said pulsed Stokes fields being provided at the same pulse repetition rate and synchronous with one another;

guiding both said pulsed pump field and said pulsed Stokes field in a collinear fashion to objective optics through at least one optical fiber;

directing both said pulsed pump field and said Stokes field through objective optics toward a focal volume in which each of said pulsed pump field said pulsed Stokes field is focused by the objective optics to generate third order non-linear coherent radiation characteristic of molecular vibrations by non-linear interaction of the pulsed pump and Stokes fields with a sample as an anti-Stokes signal, said anti-Stokes signal being generated in at least a forward direction within the sample;

collecting reflected anti-Stokes signal that is reflected off of material within the sample volume but not within the focal volume, said reflected anti-Stokes signal being collected, at least in part, by the objective optics; and guiding said reflected anti-Stokes signal toward a detector.

19. The method as claimed in claim 18, wherein said pulsed pump and Stokes fields are guided toward the objective optics via a plurality of optical fibers.

20. The method as claimed in claim 18, wherein said step of guiding said reflected anti-Stokes signal toward a detector includes guiding said reflected anti-Stokes signal through at least a portion of the optical fiber.

21. The method as claimed in claim 18, wherein said step of guiding said reflected anti-Stokes signal toward a detector includes guiding said reflected anti-Stokes signal through a plurality of optical fibers.

22. The method as claimed in claim 18, wherein said step of guiding said reflected anti-Stokes signal toward a detector also includes guiding an epi-directed anti-Stokes signal toward the detector.

23. The method as claimed in claim 18, wherein the sample is within living tissue of a subject.

24. The method as claimed in claim 18, wherein the method further includes the step of selectively directing said pulsed pump and Stokes fields toward any of a plurality of optical fibers that guide the pulsed pump and Stokes fields to the objective optics such that said pulsed pump and Stokes fields are directed toward a plurality of focal volumes within the sample volume.

25. The method as claimed in claim 18, wherein the method further includes the step of selectively directing the at least one optical fiber toward a plurality of positions within the sample such that said pulsed pump and Stokes fields are directed toward a plurality of focal volumes within the sample volume.

26. The method as claimed in claim 18, wherein the method further includes the step of selectively directing at least one return optical fiber to a plurality of positions within the sample such that said reflected anti-Stokes signal is received from a plurality of locations within the sample volume associated with said plurality of positions of the optical fiber.

* * * * *